(12) United States Patent
Ishikawa et al.

(10) Patent No.: US 10,336,708 B2
(45) Date of Patent: Jul. 2, 2019

(54) IMIDAZOLE COMPOUND, METAL SURFACE TREATMENT LIQUID, METAL SURFACE TREATMENT METHOD, AND LAMINATE PRODUCTION METHOD

(71) Applicant: TOKYO OHKA KOGYO CO., LTD., Kawasaki-shi (JP)

(72) Inventors: Tatsuro Ishikawa, Kawasaki (JP); Kunihiro Noda, Kawasaki (JP); Yasuhide Ohuchi, Kawasaki (JP); Hiroki Chisaka, Kawasaki (JP); Dai Shiota, Kawasaki (JP); Yukitsugu Maeda, Myoko (JP); Takafumi Imoto, Myoko (JP); Kouhei Fujita, Myoko (JP); Yasuyuki Akai, Himeji (JP)

(73) Assignee: TOKYO OHKA KOGYO CO., LTD., Kawasaki-Shi (JP)

( * ) Notice: Subject to any disclaimer, the term of this patent is extended or adjusted under 35 U.S.C. 154(b) by 114 days.

(21) Appl. No.: 15/506,681

(22) PCT Filed: Aug. 27, 2015

(86) PCT No.: PCT/JP2015/074280
§ 371 (c)(1),
(2) Date: Feb. 24, 2017

(87) PCT Pub. No.: WO2016/031928
PCT Pub. Date: Mar. 3, 2016

(65) Prior Publication Data
US 2017/0247334 A1 Aug. 31, 2017

(30) Foreign Application Priority Data
Feb. 18, 2015 (JP) ................. 2015-029325

(51) Int. Cl.
| | | |
|---|---|---|
| C07D 233/60 | (2006.01) | |
| C23C 22/02 | (2006.01) | |
| C23C 22/05 | (2006.01) | |
| C23F 11/00 | (2006.01) | |
| G03F 7/004 | (2006.01) | |
| G03F 7/039 | (2006.01) | |
| H05K 3/28 | (2006.01) | |
| C08K 5/3445 | (2006.01) | |
| G03F 7/031 | (2006.01) | |
| G03F 7/038 | (2006.01) | |
| G03F 7/16 | (2006.01) | |
| G03F 7/20 | (2006.01) | |
| G03F 7/32 | (2006.01) | |
| G03F 7/40 | (2006.01) | |
| H05K 1/09 | (2006.01) | |
| H05K 3/46 | (2006.01) | |

(52) U.S. Cl.
CPC .......... *C07D 233/60* (2013.01); *C08K 5/3445* (2013.01); *C23C 22/02* (2013.01); *C23C 22/05* (2013.01); *C23F 11/00* (2013.01); *G03F 7/004* (2013.01); *G03F 7/031* (2013.01); *G03F 7/038* (2013.01); *G03F 7/039* (2013.01); *G03F 7/162* (2013.01); *G03F 7/168* (2013.01); *G03F 7/20* (2013.01); *G03F 7/322* (2013.01); *G03F 7/40* (2013.01); *H05K 1/09* (2013.01); *H05K 3/28* (2013.01); *H05K 3/4644* (2013.01); *H05K 2201/032* (2013.01)

(58) Field of Classification Search
CPC .... C07D 233/60; C08K 5/3445; C23C 22/02; C23C 22/05; C23F 11/00; G03F 7/004; G03F 7/031; G03F 7/038; G03F 7/039
See application file for complete search history.

(56) References Cited

U.S. PATENT DOCUMENTS

| | | |
|---|---|---|
| 2002/0115653 A1 | 8/2002 | Mabire et al. |
| 2003/0199530 A1 | 10/2003 | Goldstein et al. |
| 2004/0122234 A1 | 6/2004 | Hauser et al. |
| 2006/0135584 A1 | 6/2006 | Imori et al. |
| 2010/0330025 A1* | 12/2010 | Messersmith ........... A61L 27/34 424/78.17 |

FOREIGN PATENT DOCUMENTS

| | | |
|---|---|---|
| CN | 1445226 A | 10/2003 |
| CN | 1243567 C | 3/2006 |
| EP | 0165780 A1 | 12/1985 |
| JP | 2000-219876 | 8/2000 |

(Continued)

OTHER PUBLICATIONS

Translation for Sumitaka (document N above—provided by IDS).*
Heller et al. "On the reactivity of imidazole carbamates and ureas and their use as esterification and amidation reagents" (2011).*
Gomaa et al. "Novel retinoic acid 4-hydroxylase (CYP26) inhibitors based on a 3-(1h-imidazole- and triazole-1-yl)-2,2-diemthyl-3-(4-(phenylamine)phenyl)propyl scaffold" (2012).*
Office Action & Search report issued in Russian Patent Application No. 2017109679, dated Jul. 13, 2018.
Office Action issued in Taiwanese Patent Application No. 106142408, dated Aug. 20, 2018.
Supplementary European search report in European Patent Application No. 15835592.5, dated Jun. 26, 2017.

(Continued)

*Primary Examiner* — Austin Murata
(74) *Attorney, Agent, or Firm* — Knobbe, Martens, Olson & Bear LLP

(57) ABSTRACT

A novel imidazole compound that yields a surface treatment liquid that is very effective at suppressing migration and oxidation of a wiring surface; a metal surface treatment liquid that contains the imidazole compound; a metal surface treatment method that uses the metal surface treatment liquid; and a laminate production method that uses the surface treatment liquid. A metal is surface-treated using the surface treatment liquid which includes a saturated fatty acid or a saturated fatty acid ester of a specific structure, in which a prescribed position is substituted by an aromatic group of a prescribed structure and an imidazolyl group that may have a substituent group.

15 Claims, No Drawings

(56) References Cited

FOREIGN PATENT DOCUMENTS

| JP | 2001-515046 | | 9/2001 |
|---|---|---|---|
| JP | 2001-525400 | | 12/2001 |
| JP | 2003-292491 | | 10/2003 |
| JP | 2004-059497 | | 2/2004 |
| JP | 2010-156043 | * | 1/2010 |
| JP | 2010-156042 | | 7/2010 |
| JP | 2010-156043 | | 7/2010 |
| JP | 2012-244005 | | 12/2012 |
| JP | 2014-101554 | | 6/2014 |
| JP | 2015-194720 | A | 11/2015 |
| WO | WO 99/08699 | A1 | 2/1999 |
| WO | WO 1999/008699 | A1 | 2/1999 |
| WO | WO 1999/029674 | A1 | 6/1999 |
| WO | WO 2008/062182 | A1 | 5/2008 |
| WO | WO 2009/153566 | | 12/2009 |
| WO | WO 2012/139010 | A1 | 10/2012 |
| WO | WO 2016/093254 | A1 | 6/2016 |

OTHER PUBLICATIONS

Diez-Barra, Enrique et al., Double Michael addition of azoles to methyl propiolate: a straightforward entry to ligands with two heterocyclic reings, Tetrahedron Letters, 2004, 45(37), pp. 6937-6939, ISSN 0040-4039, particularly, Scheme 1, Table 1, Product 5, 7.

Gomaa, Mohamed S. et al., Novel retionoicacid 4-hydroxylase (CYP26) inhibitors based on a 3-(1 Himidazol- and triazol-1-yl)-2,2-dimethyl-3-(4-(phenylamino)phenyl)propyl scaffold, Bioorganic & Medicinal Chemistry, 2012, 20(14), pp. 4201-4207, ISSN 0968-0896, particularly, Figure 1, Acheme 1, Table 1, liarozole, naphthalene inhibitor, Compound 1, 8.

Heller, Stephen T. et al., On the reactivity of imidazole carbamates and ureas and their use as esterification and amidation reagents, Tetrahedron, 2011, 67(46), pp. 8851-8859, ISSN 0040-4020, particularly, Table 4, Scheme 3, conjugate addition product 12a-12e.

Valacchi, G. et al., Wound healing properties of hyaluronan derivatives bearing ferulate residues, Journal of Materials Chemistry B, 2015, 3(36), pp. 7037-7045, ISSN 2050-7518, particularly, Scheme 1, compound 4.

STN International, 1H-Imidazole-1-propanoic acid, 2-(1-methylethyl)-β-phenyl, File Registry [online], retrieved on Oct. 27, 2015, Entered STN: Nov. 28, 2013, CAS Registry No. 1482816-18-1.

STN International, 1H-Imidazole-1-propanoic acid, 2-ethyl-β-phenyl-, File Registry [online], retrieved on Oct. 27, 2015, Entered STN: Apr. 19, 2011, CAS Registry No. 1282322-47-7.

STN International, 1H-Imidazole-1-propanoic acid, 2-methyl-β-phenyl-, File Registry [online], retrieved on Oct. 27, 2015, Entered STN: Apr. 15, 2011, CAS Registry No. 1280705-46-5.

STN International, 1H-Imidazole-1-propanoic acid, 4,5-dimethyl-β-phenyl-, File Registry [online], retrieved on Oct. 27, 2015, Entered STN: Nov. 26, 2013, CAS Registry No. 1481556-44-8.

STN International, 1H-Imidazole-1-propanoic acid, β-phenyl-, File Registry [online], retrieved on Oct. 27, 2015, Entered STN: Jun. 24, 2011, CAS Registry No. 1310251-00-3.

STN International, 1H-Imidazole-1-propanoic acid, β-phenyl-2-(2-thienyl)-, File Registry [online], retrieved on Oct. 27, 2015, Entered STN: Dec. 16, 2013, CAS Registry No. 1495791-90-6.

STN International, 1H-Imidazole-1-propanoic acid, β-phenyl-2-propyl-, File Registry [online], retrieved on Oct. 27, 2015, Entered STN: Dec. 17, 2013, CAS Registry No. 1497475-46-3.

CAS-STN registry, Dec. 17, 2013.

Office Action issued in Chinese Patent Application No. CN201580046344.9, dated Jan. 29, 2019.

* cited by examiner

IMIDAZOLE COMPOUND, METAL SURFACE TREATMENT LIQUID, METAL SURFACE TREATMENT METHOD, AND LAMINATE PRODUCTION METHOD

This application is the U.S. National Phase under 35 U.S.C. § 371 of International Application PCT/JP2015/074280, filed Aug. 27, 2015, designating the U.S., and published in Japanese as WO 2016/031928 on Mar. 3, 2016, which claims priority to Japanese Patent Application No. 2014-176645, filed Aug. 29, 2014; and Japanese Patent Application No. 2015-029325, filed Feb. 18, 2015, the entire contents of which are incorporated herein by reference.

TECHNICAL FIELD

The present invention relates to an imidazole compound; a metal surface treatment liquid containing the imidazole compound; a metal surface treatment method using the metal surface treatment liquid; and a method for producing a laminate provided with a wiring made of metal, using the metal surface treatment liquid.

BACKGROUND ART

In order to accommodate the demands such as miniaturization or advancement in performance of various electronic devices, miniaturization and high integration of printed wiring boards and various electric/electronic elements have progressed. As a result, in terms of such printed wiring boards and electric/electronic elements, metal wirings have been thinned, and the distance between wirings have been narrowed. In relation to such printed wiring boards and various electric/electronic elements, metals such as copper, silver, tin, lead, zinc, aluminum, nickel, gold, or alloys thereof, which are excellent in conductivity and workability, have been widely used as materials for the wiring.

When printed wiring boards and electric/electronic elements are processed into various devices, the wiring made of metal is often heated once or plural times by surface mounting, or a baking treatment in the case where an insulating layer is formed on a circuit using a photosensitive composition or the like. The heating of a wiring made of metal has the following problems.

First, there is a problem that a surface of the wiring is oxidized by the heating of the wiring. Since metal is widely different from metal oxide in resistance values, when a surface of the circuit is oxidized, electric resistance of the circuit is likely to vary. Such variation in electric resistance of the circuit exerts a large influence on the performance of the product. When the surface of the circuit is oxidized, wettability between solder and the surface of the circuit deteriorates, leading to difficulty in soldering on the circuit.

When the wiring made of metal is heated, dendritic crystals made of a metal compound are likely to be formed as a result of elution (migration) of metal ions on a surface of the substrate due to moisture of a surface of the wiring. When the distance between the wirings is small, there is a problem that dendritic crystals made of the metal compound are formed by migration, and thus short circuit of the wiring is likely to occur.

In order to solve the problems mentioned above, there has been proposed a method in which metal is subjected to a surface treatment before heating. Specifically, there has been proposed a method in which a wiring made of copper or an alloy containing copper is subjected to a surface treatment using a surface treatment liquid containing an imidazole compound, iron ions, and a phosphonic acid-based chelating agent (Patent Document 1), and a method in which a wiring made of copper or an alloy containing copper is subjected to a surface treatment using an aqueous solution of an azole compound as a surface treatment liquid (Patent Document 2).

Patent Document 1: Japanese Unexamined Patent Application, Publication No. 2014-101554
Patent Document 2: Japanese Unexamined Patent Application, Publication No. 2012-244005

DISCLOSURE OF THE INVENTION

Problems to be Solved by the Invention

However, in some cases, even such a treatment using the surface treatment liquid as disclosed in Patent Documents 1 and 2 cannot satisfactorily suppress migration and oxidization of a surface of a wiring, depending on the temperature for heating the wiring, and the number of heating operations. Therefore, there is a need for a surface treatment liquid, and a metal surface treatment method using the surface treatment liquid in which the effect of suppressing migration and oxidization of a surface of the wiring surface has been further enhanced.

The present invention has been made in light of the problems mentioned above, and an object thereof is to provide a novel imidazole compound which gives a metal surface treatment liquid having excellent effect of suppressing migration and oxidization of a surface of a wiring; a metal surface treatment liquid containing the imidazole compound; a metal surface treatment method using the metal surface treatment liquid; and a method for producing a laminate using the metal surface treatment liquid.

Means for Solving the Problems

The present inventors have found that the object mentioned above can be achieved by subjecting metal to surface treatment using a metal surface treatment liquid containing a saturated fatty acid or saturated fatty acid ester having a specific structure in which an aromatic group having a predetermined structure and an optionally substituted imidazolyl group are substituted at a predetermined position, thus completing the present invention. Specifically, the present invention provides the following.

A first aspect of the present invention provides an imidazole compound represented by the following formula (1a):

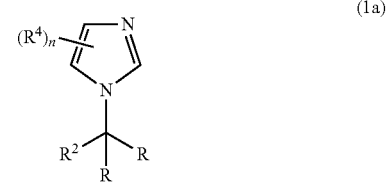

(1a)

in the formula, R each independently represents a hydrogen atom or a monovalent organic group; $R^2$ represents an optionally substituted aromatic group; $R^4$ each independently represents a halogen atom, a hydroxy group, a mercapto group, a sulfide group, a silyl group, a silanol group, a nitro group, a nitroso group, a sulfonato group, a phosphino group, a phosphinyl group, a phosphonato group, or an organic group; and n represents an integer of 0 to 3. R mentioned above may be bonded to the other R or $R^2$ to form a cyclic structure.

A second aspect of the present invention provides a metal surface treatment liquid containing the imidazole compound according to the first aspect.

A third aspect of the present invention provides a metal surface treatment method, which includes bringing the metal surface treatment liquid according the second aspect into contact with the metal.

A fourth aspect of the present invention provides a method for producing a laminate, in which the method includes: a chemical conversion coating film formation step of bringing a wired substrate, the wired substrate including a substrate and a wiring made of metal to be disposed on the substrate, into contact with the metal surface treatment liquid according to the second aspect, thereby forming a chemical conversion coating film on a surface of the wiring; and an insulating layer formation step of forming an insulating layer on a surface provided with the chemical conversion coating film of the wired substrate.

A fifth aspect of the present invention provides a method for producing a laminate, in which the method includes a chemical conversion coating film formation step of bringing a laminate provided with an exposed wiring, the laminate including a substrate, a wiring made of metal to be disposed on the substrate, and an insulating layer which is disposed on the substrate and covers the wiring so that the wiring is partially exposed, into contact with the metal surface treatment liquid according to the second aspect, thereby forming a chemical conversion coating film on a surface of the wiring exposed from the insulating layer.

Effects of the Invention

According the present invention, it is possible to provide a novel imidazole compound which gives a metal surface treatment liquid having excellent effect of suppressing migration and oxidization of a surface of a wiring; a metal surface treatment liquid containing the imidazole compound; a metal surface treatment method using the metal surface treatment liquid; and a method for producing a laminate using the metal surface treatment liquid.

PREFERRED MODE FOR CARRYING OUT THE INVENTION

<<Imidazole Compound>>

A first aspect of the present invention is directed to an imidazole compound represented by the following formula (1a). When the imidazole compound represented by the formula (1a) is brought into contact with metal, the imidazole compound represented by the formula (1a) reacts with metal ions to form a chemical conversion coating film on a surface of metal. When the chemical conversion coating film is formed on a surface of a wiring made of metal, short circuit between wirings due to migration of the metal, and oxidization of the metal are suppressed.

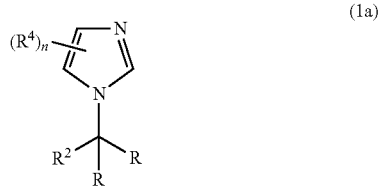

(1a)

In the formula, R each independently represents a hydrogen atom or a monovalent organic group; $R^2$ represents an optionally substituted aromatic group; $R^4$ each independently represents a halogen atom, a hydroxy group, a mercapto group, a sulfide group, a silyl group, a silanol group, a nitro group, a nitroso group, a sulfonato group, a phosphino group, a phosphinyl group, a phosphonato group, or an organic group; and n represents an integer of 0 to 3. R mentioned above may be bonded to the other R or $R^2$ to form a cyclic structure.

In the formula (1a), R is a hydrogen atom or a monovalent organic group. The monovalent organic group is not particularly limited, and may be, for example, an optionally substituted alkyl group, an optionally substituted aromatic group or the like, and this alkyl group may contain an ester bond or the like in the chain. The alkyl group may be, for example, the same as $R^1$ in the formula (1) mentioned below, and the number of carbon atoms is preferably 1 to 40, more preferably 1 to 30, still more preferably 1 to 20, and yet preferably 1 to 10. The substituent, which the alkyl group may have, may be the same as the substituent, which the alkylene group as $R^3$ in the formula (1) may have. The optionally substituted aromatic group is the same as $R^2$ in the formula (1) mentioned below, and is preferably an aryl group, and more preferably a phenyl group. The optionally substituted aromatic group as R may be the same as or different from $R^2$. In the formula (1a), one R is preferably a hydrogen atom, and more preferably, one R is a hydrogen atom and the other R is an optionally substituted alkyl group or an optionally substituted aromatic group. In the formula (1a), R may be bonded to the other R or $R^2$ to form a cyclic structure; for example, when at least one R is an optionally substituted alkyl group, R may be bonded to the other R or $R^2$ to form a cyclic structure.

The imidazole compound may be a compound represented by the following formula (1).

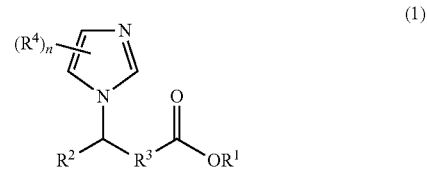

(1)

In the formula (1), $R^1$ is a hydrogen atom or an alkyl group; $R^2$ is an optionally substituted aromatic group; $R^3$ is an optionally substituted alkylene group; $R^4$ is a halogen atom, a hydroxy group, a mercapto group, a sulfide group, a silyl group, a silanol group, a nitro group, a nitroso group, a sulfonato group, a phosphino group, a phosphinyl group, a phosphonato group, or an organic group; and n is an integer of 0 to 3. $R^3$ may be bonded to the other $R^2$ to form a cyclic structure.

In the formula (1), $R^1$ is a hydrogen atom or an alkyl group. When $R^1$ is an alkyl group, the alkyl group may be either a linear alkyl group or a branched alkyl group. The number of carbon atoms of the alkyl group is not particularly limited, but is preferably 1 to 20, more preferably 1 to 10, and still more preferably 1 to 5.

Specific examples of the alkyl group suitable as $R^1$ include a methyl group, an ethyl group, an n-propyl group, an isopropyl group, an n-butyl group, an isobutyl group, an sec-butyl group, a tert-butyl group, an n-pentyl group, an isopentyl group, a tert-pentyl group, an n-hexyl group, an n-heptyl group, an n-octyl group, a 2-ethyl-n-hexyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, an n-nonadecyl group, and an n-icosyl group.

In the formula (1), $R^2$ is an optionally substituted aromatic group. The optionally substituted aromatic group may be either an optionally substituted aromatic hydrocarbon group or an optionally substituted aromatic heterocyclic group.

The type of the aromatic hydrocarbon group is not particularly limited without interfering with the object of the present invention. The aromatic hydrocarbon group may be a monocyclic aromatic group, may be formed by fusion of two or more aromatic hydrocarbon groups, or may be formed by bonding of two or more aromatic hydrocarbon groups through a single bond. The aromatic hydrocarbon group is preferably a phenyl group, a naphthyl group, a biphenylyl group, an anthryl group, or a phenanthrenyl group.

The type of the aromatic heterocyclic group is not particularly limited without interfering with the object of the present invention. The aromatic heterocyclic group may be either a monocyclic group or a polycyclic group. The aromatic heterocyclic group is preferably a pyridyl group, a furyl group, a thienyl group, an imidazolyl group, a pyrazolyl group, an oxazolyl group, a thiazolyl group, an isoxazolyl group, an isothiazolyl group, a benzoxazolyl group, a benzothiazolyl group, and a benzoimidazolyl group.

Examples of the substituent, which a phenyl group, a polycyclic aromatic hydrocarbon group, or an aromatic heterocyclic group may have, include a halogen atom, a hydroxy group, a mercapto group, a sulfide group, a silyl group, a silanol group, a nitro group, a nitroso group, a sulfino group, a sulfo group, a sulfonato group, a phosphino group, a phosphinyl group, a phosphono group, a phosphonato group, an amino group, an ammonio group, and an organic group. When the phenyl group, the polycyclic aromatic hydrocarbon group, or the aromatic heterocyclic group have plural substituents, the plural substituents may be the same or different.

When the substituent, which the aromatic group has, is an organic group, examples of the organic group include an alkyl group, an alkenyl group, a cycloalkyl group, a cycloalkenyl group, an aryl group, an aralkyl group, or the like. This organic group may have a bond or a substituent, other than a hydrocarbon group such as a heteroatom, in the organic group. This organic group may be either linear, branched, or cyclic. This organic group is usually monovalent, but can be a divalent or higher polyvalent organic group when forming a cyclic structure.

When the aromatic group has a substituent on neighboring carbon atoms, two substituents bonded on neighboring carbon atoms may be bonded to form a cyclic structure. Examples of the cyclic structure include an aliphatic hydrocarbon ring, and an aliphatic ring having a heteroatom.

When the substituent, which the aromatic group has, is an organic group, the bond included in the organic group is not particularly limited, without impairing the effect of the present invention; and the organic group may include a bond having a heteroatom such as an oxygen atom, a nitrogen atom, or a silicon atom. Specific examples of the bonded containing a heteroatom include, an ether bond, a thioether bond, a carbonyl bond, a thiocarbonyl bond, an ester bond, an amide bond, an amino bond (—$NR^A$—: $R^A$ represents a hydrogen atom or a monovalent organic group), a urethane bond, an imino bond (—N=C(—$R^B$)—, —C(=$NR^B$)—: $R^B$ represents a hydrogen atom or a monovalent organic group), a carbonate bond, a sulfonyl bond, a sulfinyl bond, an azo bond, and the like.

From the viewpoint of heat resistance of the imidazole compound represented by the formula (1a) or (1), the bond containing a heteroatom, which an organic group may have, is preferably an ether bond, a thioether bond, a carbonyl bond, a thiocarbonyl bond, an ester bond, an amide bond, an amino bond (—$NR^A$—: $R^A$ represents a hydrogen atom or a monovalent organic group), an urethane bond, an imino bond (—N=C(—$R^B$)—, —C(=$NR^B$)—: $R^B$ represents a hydrogen atom or a monovalent organic group), a carbonate bond, a sulfonyl bond, or a sulfinyl bond.

When the organic group is a substituent other than the hydrocarbon group, the type of the substituent other than the hydrocarbon group is not particularly limited without interfering with the object of the present invention. Specific examples of the substituent other than the hydrocarbon group include a halogen atom, a hydroxy group, a mercapto group, a sulfide group, a cyano group, an isocyano group, a cyanato group, an isocyanato group, a thiocyanato group, an isothiocyanato group, an silyl group, an silanol group, an alkoxy group, an alkoxycarbonyl group, an amino group, a monoalkylamino group, a dialkylamino group, a monoarylamino group, a diarylamino group, a carbamoyl group, a thiocarbamoyl group, a nitro group, a nitroso group, a carboxylate group, an acyl group, an acyloxy group, a sulfino group, a sulfonato group, a phosphino group, a phosphinyl group, a phosphonato group, an alkyl ether group, an alkenyl ether group, an alkyl thioether group, an alkenyl thioether group, an aryl ether group, an aryl thioether group, and the like. The hydrogen atom included in the substituent mentioned above may be substituted with a hydrocarbon group. The hydrocarbon group included in the substituent mentioned above may be either linear, branched, or cyclic.

The substituent, which a phenyl group, a polycyclic aromatic hydrocarbon group, or an aromatic heterocyclic group has, is preferably an alkyl group having 1 to 12 carbon atoms, an aryl group having 1 to 12 carbon atoms, an alkoxy group having 1 to 12 carbon atoms, an aryloxy group having 1 to 12 carbon atoms, an arylamino group having 1 to 12 carbon atoms, and a halogen atom.

$R^2$ is preferably an optionally substituted phenyl group, an optionally substituted furyl group, or an optionally substituted thienyl group, since an imidazole compound represented by the formula (1a) or (1) can be synthesized inexpensively and easily, and the imidazole compound has satisfactory solubility in water or an organic solvent.

In the formula (1), $R^3$ is an optionally substituted alkylene group. The substituent, which an alkylene group may have, is not particularly limited, without interfering with the object of the present invention. Specific examples of the substituent, which an alkylene group may have, include a hydroxy group, an alkoxy group, an amino group, a cyano group, a halogen atom, and the like. The alkylene group may be either a linear alkylene group or a branched alkylene group, and is preferably a linear alkylene group. The number of carbon atoms of the alkylene group is not particularly limited, but is preferably 1 to 20, more preferably 1 to 10, and still more preferably 1 to 5. Note that the number of carbon atoms of the alkylene group does not include the number of carbon atoms of the substituent bonded to an alkylene group.

The alkoxy group as the substituent bonded to the alkylene group may be either a linear alkoxy group or a branched alkoxy group. The number of carbon atoms of the alkoxy group as the substituent is not particularly limited, but is preferably 1 to 10, more preferably 1 to 6, and particularly preferably 1 to 3.

The amino group as the substituent bonded to the alkylene group may be a monoalkylamino group or a dialkylamino group. The alkyl group included in the monoalkylamino group or dialkylamino group may be either a linear alkyl group or a branched alkyl group. The number of carbon atoms of the alkyl group included in the monoalkylamino group or dialkylamino group is not particularly limited, but is preferably 1 to 10, more preferably 1 to 6, and particularly preferably 1 to 3.

Specific examples of the alkylene group suitable as $R^3$ include a methylene group, an ethane-1,2-diyl group, an n-propane-1,3-diyl group, an n-propane-2,2-diyl group, an n-butane-1,4-diyl group, an n-pentane-1,5-diyl group, an n-hexane-1,6-diyl group, an n-heptane-1,7-diyl group, an n-octane-1,8-diyl group, an n-nonane-1,9-diyl group, an n-decane-1,10-diyl group, an n-undecane-1,11-diyl group, an n-dodecane-1,12-diyl group, an n-tridecane-1,13-diyl group, an n-tetradecane-1,14-diyl group, an n-pentadecane-1,15-diyl group, an n-hexadecane-1,16-diyl group, an n-heptadecane-1,17-diyl group, an n-octadecane-1,18-diyl group, an n-nonadecane-1,19-diyl group, and an n-icosane-1,20-diyl group.

$R^4$ is a halogen atom, a hydroxy group, a mercapto group, a sulfide group, a silyl group, a silanol group, a nitro group, a nitroso group, a sulfonato group, a phosphino group, a phosphinyl group, a phosphonato group, or an organic group, and n is an integer of 0 to 3. When n is an integer of 2 to 3, plural $R^4$(s) may be the same or different.

When $R^4$ is an organic group, the organic group is the same as an organic group, which an aromatic group may have as a substituent, as for $R^2$.

When $R^4$ is an organic group, the organic group is preferably an alkyl group, an aromatic hydrocarbon group, and an aromatic heterocyclic group. The alkyl group is preferably a linear or branched alkyl group having 1 to 8 carbon atoms, and more preferably a methyl group, an ethyl group, an n-propyl group, and an isopropyl group. The aromatic hydrocarbon group is preferably a phenyl group, a naphthyl group, a biphenylyl group, an anthryl group, and a phenanthrenyl group, more preferably a phenyl group and a naphthyl group, and particularly preferably a phenyl group. The aromatic heterocyclic group is preferably a pyridyl group, a furyl group, a thienyl group, an imidazolyl group, a pyrazolyl group, an oxazolyl group, a thiazolyl group, an isoxazolyl group, an isothiazolyl group, a benzoxazolyl group, a benzothiazolyl group, and a benzoimidazolyl group, and more preferably a furyl group and a thienyl group.

When $R^4$ is an alkyl group, the position of the alkyl group bonding on an imidazole ring is preferably any one of 2-, 4-, and 5-positions, and more preferably 2-position. When $R^4$ is an aromatic hydrocarbon group and an aromatic heterocyclic group, the position of these groups bonding on imidazole is preferably 2-position.

Among the above-mentioned imidazole compounds represented by the formula (1a), a compound represented by the following formula (1-1a) is preferable, since it can be synthesized inexpensively and easily.

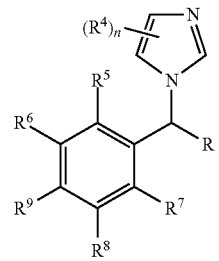

(1-1a)

In the formula (1-1a), R, $R^4$, and n are the same as those in defined the formula (1a); and $R^5$, $R^6$, $R^7$, $R^8$, and $R^9$ are each independently a hydrogen atom, a halogen atom, a hydroxy group, a mercapto group, a sulfide group, a silyl group, a silanol group, a nitro group, a nitroso group, a sulfino group, a sulfo group, a sulfonato group, a phosphino group, a phosphinyl group, a phosphono group, a phosphonato group, an amino group, an ammonio group, or an organic group, provided that at least one of $R^5$, $R^6$, $R^7$, $R^8$, and $R^9$ is a group other than a hydrogen atom. At least two of $R^5$, $R^6$, $R^7$, $R^8$, and $R^9$ may be bonded to form a cyclic structure. R may be bonded to $R^7$ to form a cyclic structure.

$R^5$, $R^6$, $R^7$, $R^8$, and $R^9$ are the same as those defined in the formula (1-1) mentioned below. In the formula (1-1a), R may be bonded to $R^7$ to form a cyclic structure; for example, when R is an optionally substituted alkyl group, R may be bonded to $R^7$ to form a cyclic structure.

Among imidazole compounds represented by the formula (1) or (1-1a), a compound represented by the following formula (1-1) is preferable, and a compound represented by the formula (1-1), in which $R^3$ is a methylene group, is more preferable, since these compounds can be synthesized inexpensively and easily, and have excellent solubility in water or an organic solvent.

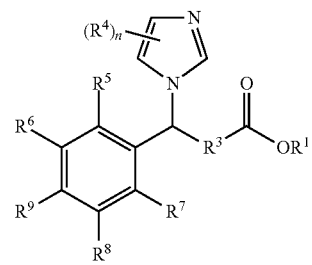

(1-1)

In the formula (1-1), $R^1$, $R^3$, $R^4$, and n are the same as those defined in the formula (1); and $R^5$, $R^6$, $R^2$, $R^8$, and $R^9$ are each independently a hydrogen atom, a halogen atom, a hydroxy group, a mercapto group, a sulfide group, a silyl group, a silanol group, a nitro group, a nitroso group, a sulfino group, a sulfo group, a sulfonato group, a phosphino group, a phosphinyl group, a phosphono group, a phosphonato group, an amino group, an ammonio group, or an organic group, provided that at least one of $R^5$, $R^6$, $R^2$, $R^8$, and $R^9$ is a group other than a hydrogen atom. At least two of $R^5$, $R^6$, $R^2$, $R^8$, and $R^9$ may be bonded to form a cyclic structure. $R^3$ may be bonded to $R^2$ to form a cyclic structure.

When $R^5$, $R^6$, $R^2$, $R^8$, and $R^9$ are organic groups, the organic group is the same as an organic group, which $R^2$ in the formula (1) has as a substituent. $R^5$, $R^6$, $R^2$, and $R^8$ are preferably hydrogen atoms in view of solubility of an imidazole compound in solvent.

Among these, at least one of $R^5$, $R^6$, $R^7$, $R^8$, and $R^9$ is preferably the following substituent; and $R^9$ is particularly preferably the following substituent. When $R^9$ is the following substituent, $R^5$, $R^6$, $R^7$, and $R^8$ are preferably hydrogen atom.

($R^{10}$ is a hydrogen atom or an organic group.)

When $R^{10}$ is an organic group, the organic group is the same as an organic group, which $R^2$ in the formula (1) has as a substituent. $R^{10}$ is preferably an alkyl group, more preferably, an alkyl group having 1 to 8 carbon atoms, particularly preferably an alkyl group having 1 to 3 carbon atoms, and most preferably a methyl group.

Among the compounds represented by the formula (1-1) mentioned above, a compound represented by the following formula (1-1-1) is preferable.

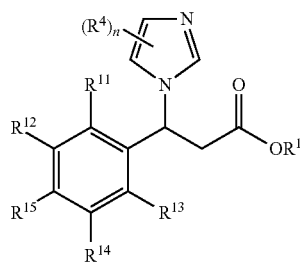

(1-1-1)

In the formula (1-1-1), $R^1$, $R^4$, and n are the same as those defined in the formula (1); and $R^{11}$, $R^{12}$, $R^{13}$, $R^{14}$, and $R^{15}$ are each independently a hydrogen atom, a hydroxy group, a mercapto group, a sulfide group, a silyl group, a silanol group, a nitro group, a nitroso group, a sulfino group, a sulfo group, a sulfonato group, a phosphino group, a phosphinyl group, a phosphono group, a phosphonato group, an amino group, an ammonio group, or an organic group, provided that at least one of $R^{11}$, $R^{12}$, $R^{13}$, $R^{14}$, and $R^{15}$ is a group other than a hydrogen atom.

Among the compounds represented by the formula (1-1-1), at least one of $R^{11}$, $R^{12}$, $R^{13}$, $R^{14}$, and $R^{15}$ is preferably represented by the above-mentioned —O—$R^{10}$; and $R^{15}$ is particularly preferably a group represented by —O—$R^{10}$. When $R^{15}$ is a group represented by —O—$R^{10}$, $R^{11}$, $R^{12}$, $R^{13}$, and $R^{14}$ are preferably hydrogen atoms.

The method for synthesizing the above-mentioned imidazole compound represented by the formula (1a) is not particularly limited. For example, imidazolylation is performed by reacting a halide represented by $R^2CR(Hal)R$ ($R^2$ and R are the same as those defined in the formula (1a), and Hal is a halogen atom) with the below-mentioned imidazole compound represented by the formula (II) in accordance with a conventional method, thereby making it possible to synthesize the above-mentioned imidazole compound represented by the formula (1a).

The method for synthesizing the above-mentioned imidazole compound represented by the formula (1) is not particularly limited. For example, imidazolylation is performed by reacting a halogen-containing carboxylic acid derivative represented by the following formula (I) with an imidazole compound represented by the following formula (II) in accordance with a conventional method, thereby making it possible to synthesize the above-mentioned imidazole compound represented by the formula (1).

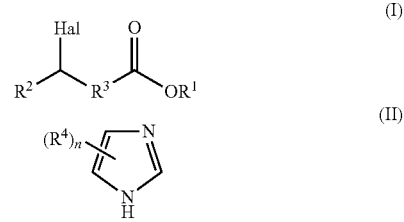

In the formulas (I) and (II), $R^1$, $R^2$, $R^3$, $R^4$, and n are the same as those defined in the formula (1). In the formula (I), Hal is a halogen atom.

When the imidazole compound is a compound represented by the formula (1) in which $R^3$ is a methylene group, that is, the imidazole compound is a compound represented by the following formula (1-2), it is also possible to synthesize the imidazole compound by the Michael addition reaction which will be described below.

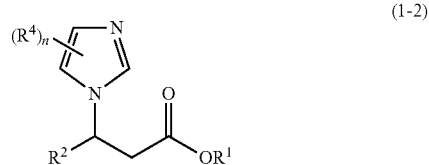

(1-2)

In the formula (1-2), $R^1$, $R^2$, $R^4$, and n are the same as those defined in the formula (1).

Specifically, for example, a 3-substituted acrylic acid derivative represented by the following formula (III) is mixed with an imidazole compound represented by the above-mentioned formula (II) in a solvent to cause a Michael addition reaction, thereby obtaining an imidazole compound represented by the above-mentioned formula (1-2).

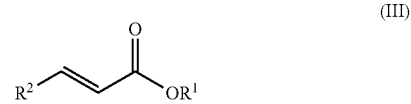

(III)

In the formula (III), $R^1$ and $R^2$ are the same as those defined in the formula (1).

3-Substituted acrylic acid derivative having an imidazolyl group represented by the following formula (IV) is added in a solvent containing water, thereby obtaining an imidazole compound represented by the following formula (1-3).

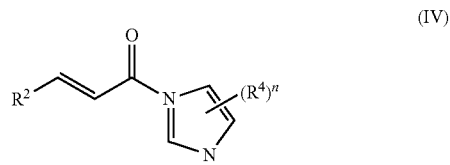

(IV)

-continued

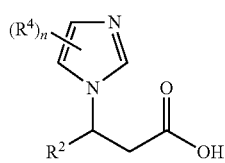
(1-3)

In the formulas (IV) and (1-3), $R^2$, $R^4$, and n are the same as those defined in the formula (1).

In this case, hydrolysis of the above-mentioned 3-substituted acrylic acid derivative represented by the formula (IV) leads to production of the above-mentioned imidazole compound represented by the formula (II) and 3-substituted acrylic acid represented by the following formula (V). Then, the Michael addition reaction occurs between the 3-substituted acrylic acid represented by the following formula (V) and the above-mentioned imidazole compound represented by the formula (II) to produce the above-mentioned imidazole compound represented by the formula (1-3).

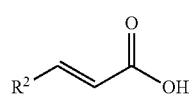
(V)

In the formula (V), $R^2$ is the same as those defined in the formula (1).

Suitable specific examples of the imidazole compound represented by the formula (1a) or (1) include the following.

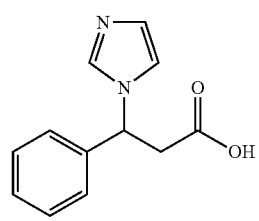

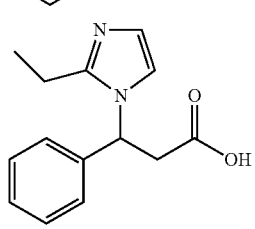

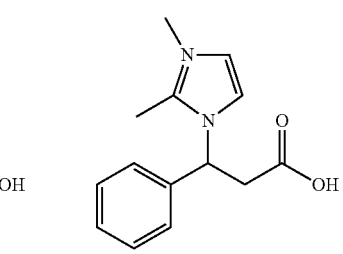

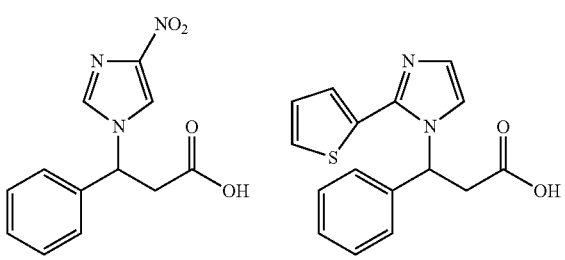

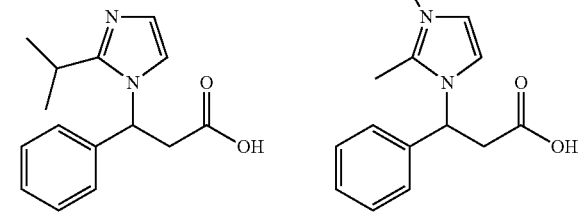

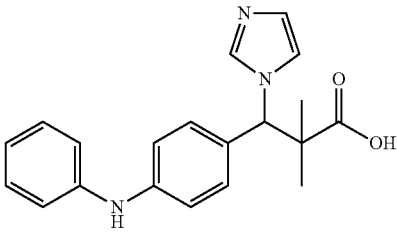

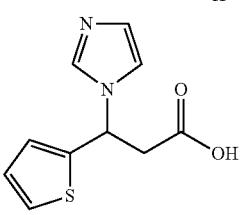

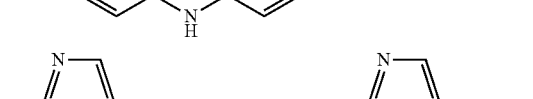

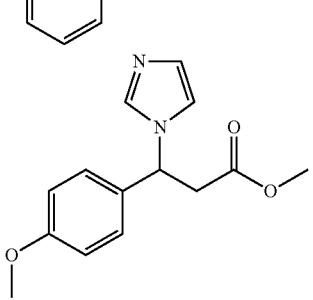

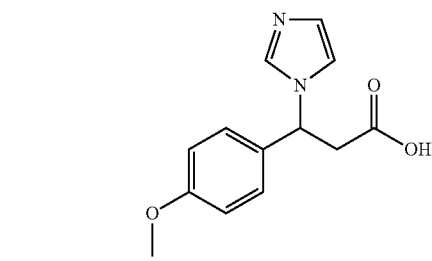

-continued

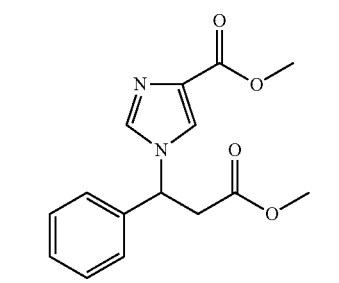
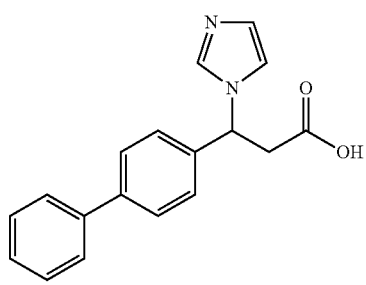
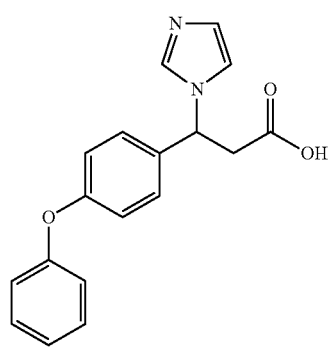
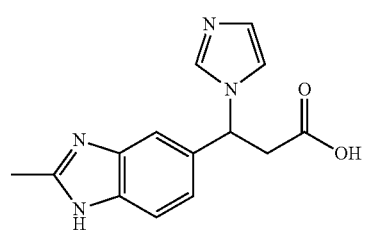
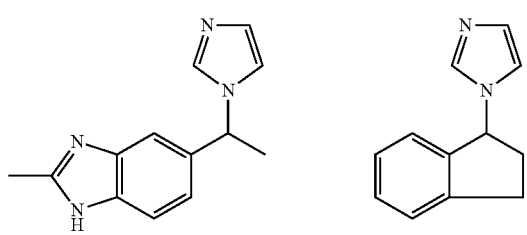
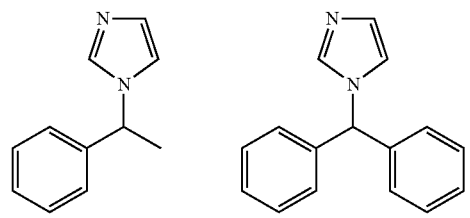

-continued

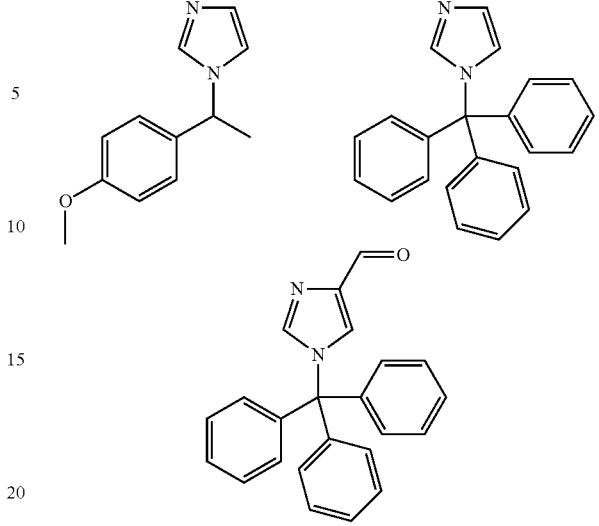

<<Metal Surface Treatment Liquid>>

The second aspect of the present invention is directed to a metal surface treatment liquid containing the above-mentioned imidazole compound represented by the formula (1a). When the metal surface treatment liquid is brought into contact with metal, the imidazole compound represented by the formula (1a) reacts with metal ions to form a chemical conversion coating film on a surface of the metal. When the chemical conversion coating film is formed on a surface of a wiring made of metal, short circuit between wirings due to migration of the metal, and oxidization of the metal are suppressed.

The metal surface treatment liquid may also contain a resin. Inclusion of the resin in the metal surface treatment liquid enables adjustment of coatability of the metal surface treatment liquid, and formation of a resin film having a function of insulation property on the metal using the metal surface treatment liquid. The type of the resin is not particularly limited, as long as the resin is soluble in solvents mentioned below.

When the metal surface treatment liquid contains an insulating resin, a chemical conversion coating film by bringing the metal into contact with the metal surface treatment liquid, and then the solvent is removed, thereby making it possible to form an insulating film on the metal. When a surface treatment of the metal and formation of an insulating film on the metal are performed using a metal surface treatment liquid without containing resin, coating with the metal surface treatment liquid and coating with a coating solution for forming an insulating film are required. Meanwhile, when using a metal surface treatment liquid containing an insulating resin, a surface treatment of the metal and formation of an insulating film on the metal can be performed by single coating of the metal surface treatment liquid.

The metal surface treatment liquid may also be a liquid prepared by adding an imidazole compound represented by the formula (1a) to a photoresist composition. In this case, the photoresist composition may contain a resin or not. When the photoresist composition includes no resin, it is preferable for the photoresist composition to contain a polymerizable low-molecular weight compound capable of increasing the molecular weight under exposure. When the metal surface treatment liquid is a photoresist composition containing an imidazole compound represented by the formula (1a), it is possible to form a pattern having a function such as insulation property on metal by photolithography while performing a surface treatment of the metal. The type of the photoresist composition is not particularly limited, but can be appropriately selected from photoresist compositions which have hitherto been used for various purposes. The photoresist composition may be either a positive photoresist composition or a negative photoresist composition.

The metal to be treated with the metal surface treatment liquid is not particularly limited, but is preferably copper, silver, gold, tin, lead, zinc, aluminum, nickel, palladium, and chromium, and alloys thereof. The metal to be treated is preferably copper or an alloy containing copper because of its particularly satisfactory effect of suppressing migration of the metal due to the surface treatment liquid and oxidation of the metal surface. The metal contained in the alloy containing copper, other than copper, is not particularly limited, but is preferably one or more metals selected from the group consisting of silver, gold, tin, lead, zinc, aluminum, nickel, palladium, and chromium.

In the metal surface treatment liquid, an imidazole compound represented by the formula (1a) is dissolved in a solvent. The type of the solvent is not particularly limited, as long as the solvent can dissolve the imidazole compound represented by the formula (1a) in a desired concentration, and the solvent may be either water, an organic solvent, or an aqueous solution of an organic solvent. The solvent is preferably water in that it can prepare a metal surface treatment liquid inexpensively. The solvent is preferably an organic solvent, from the viewpoint of its capability of easily dissolving an imidazole compound in a satisfactory manner, regardless of the type of the imidazole compound.

Suitable examples of the organic solvent to be used as the solvent include glycol monoethers such as ethylene glycol monomethyl ether, ethylene glycol monoethyl ether, ethylene glycol monopropyl ether, ethylene glycol monobutyl ether, propylene glycol monomethyl ether, propylene glycol monoethyl ether, propylene glycol monopropyl ether, propylene glycol monobutyl ether, diethylene glycol monomethyl ether, diethylene glycol monoethyl ether, diethylene glycol monopropyl ether, and diethylene glycol monophenyl ether; glycol diethers such as ethylene glycol dimethyl ether, ethylene glycol diethyl ether, ethylene glycol dipropyl ether, propylene glycol dimethyl ether, propylene glycol diethyl ether, propylene glycol dipropyl ether, diethylene glycol dimethyl ether, diethylene glycol diethyl ether, and diethylene glycol dipropyl ether; glycol monoacetates such as ethylene glycol monomethyl ether acetate, ethylene glycol monoethyl ether acetate, ethylene glycol monopropyl ether acetate, ethylene glycol monobutyl ether acetate, ethylene glycol monophenyl ether acetate, diethylene glycol monomethyl ether acetate, and diethylene glycol monoethyl ether acetate; monoether monoacetates of diols, such as diethylene glycol monopropyl ether acetate, diethylene glycol monobutyl ether acetate, diethylene glycol monophenyl ether acetate, propylene glycol monomethyl ether acetate, propylene glycol monoethyl ether acetate, propylene glycol monopropyl ether acetate, 2-methoxybutyl acetate, 3-methoxybutyl acetate, 4-methoxybutyl acetate, 2-methyl-3-methoxybutyl acetate, 3-methyl-3-methoxybutyl acetate, 3-ethyl-3-methoxybutyl acetate, 2-ethoxybutyl acetate, 4-ethoxybutyl acetate, 4-propoxybutyl acetate, 2-methoxypentyl acetate, 3-methoxypentyl acetate, 4-methoxypentyl acetate, 2-methyl-3-methoxypentyl acetate, 3-methyl-3-methoxypentyl acetate, 3-methyl-4-methoxypentyl acetate, and 4-methyl-4-methoxypentyl acetate; ketones such as acetone, methyl ethyl ketone, diethyl ketone, methyl isobutyl ketone, ethyl isobutyl ketone, and cyclohexanone; esters such as methyl propionate, ethyl propionate, propyl propionate, isopropyl propionate, 2-hydroxymethyl propionate, 2-hydroxyethyl propionate, 2-hydroxy-2-methyl, methyl-3-methoxypropionate, ethyl-3-methoxypropionate, ethyl-3-ethoxypropionate, ethyl-3-propoxypropionate, propyl-3-methoxypropionate, isopropyl-3-methoxypropionate, ethoxyethyl acetate, oxyethyl acetate, methyl 2-hydroxy-3-methylbutanoate, methyl acetate, ethyl acetate, propyl acetate, isopropyl acetate, butyl acetate, isoamyl acetate, methyl carbonate, ethyl carbonate, propyl carbonate, butyl carbonate, methyl pyruvate, ethyl pyruvate, propyl pyruvate, butyl pyruvate, methyl acetoacetate, ethyl acetoacetate, benzyl acetate, ethyl benzoate, diethyl oxalate, diethyl maleate, and γ-butyrolactone; ethers such as diethyl ether, dipropyl ether, dibutyl ether, dihexyl ether, benzyl methyl ether, benzyl ethyl ether, and tetrahydrofuran; aromatic compounds such as benzene, toluene, xylene, ethylbenzene, cresol, and chlorobenzene; aliphatic alcohols such as methanol, ethanol, n-propanol, isopropanol, n-butanol, n-hexanol, and cyclohexanol; glycols such as ethylene glycol, diethylene glycol, propylene glycol, and dipropylene glycol; glycerol; and aprotic polar organic solvents such as N,N,N',N'-tetramethylurea, N-methyl-2-pyrrolidone, N,N-dimethylformamide, N,N-dimethylacetamide, hexamethylphosphoramide, 1,3-dimethyl-2-imidazolidinone, and dimethyl sulfoxide.

The concentration of the imidazole compound represented by the formula (1a) in the metal surface treatment liquid is not particularly limited, without interfering with the object of the present invention. The concentration of the imidazole compound represented by the formula (1a) in the metal surface treatment liquid is preferably 0.01 to 10% by mass, more preferably 0.01 to 7% by mass, particularly preferably 0.1 to 5% by mass, and most preferably 0.5 to 3% by mass, based on the mass of the metal surface treatment liquid.

The metal surface treatment liquid may contain various additives other than the compound represented by the formula (1a), without interfering with the object of the present invention. Examples of the additive, which the metal surface treatment liquid may contain, include a pH adjustor, a surfactant, a preservative, a viscosity modifier, an antioxidant, an ultraviolet absorber, a colorant, and the like. These additives are used in the amount in which these additives are usually used, without interfering with the object of the present invention.

The metal surface treatment liquid may contain an organic base having a triazole skeleton. Examples of the organic base having a triazole skeleton include triazole, benzotriazole, 1H-benzotriazole-5-carboxylic acid, and the like. Mixing of these organic bases in the metal surface treatment liquid can enhance the effect of suppressing formation of an oxide film when metal is treated with the metal surface treatment liquid. The content of the organic base in the metal surface treatment liquid is preferably 0.01 to 5% by mass, and more preferably 0.01 to 3.5% by mass. The content is still more preferably 0.1 to 2.5% by mass, and particularly preferably 0.25 to 1.5% by mass.

The metal surface treatment liquid may also contain a halogen compound or a zinc compound. When the metal surface treatment liquid contains the halogen compound or zinc compound, heat resistance of a chemical conversion coating film to be formed by a treatment with a metal surface treatment liquid is improved.

Specific examples of the halogen compound include sodium fluoride, potassium fluoride, ammonium fluoride, sodium chloride, potassium chloride, ammonium chloride, 2-chloropropionic acid, 3-chloropropionic acid, sodium bromide, potassium bromide, ammonium bromide, 2-bromopropionic acid, 3-bromopropionic acid, sodium iodide, potassium iodide, ammonium iodide, 2-iodopropionic acid, and 3-iodopropionic acid. A combination of two or more halogen compounds may be mixed in the metal surface treatment liquid. The content of the halogen compound in the metal surface treatment liquid is preferably 0.001 to 1% by mass, and more preferably 0.01 to 0.1% by mass.

Specific examples of the zinc compound include zinc oxide, zinc formate, zinc acetate, zinc oxalate, zinc lactate, zinc citrate, zinc sulfate, zinc nitrate, zinc phosphate, zinc chloride, zinc bromide, and zinc iodide. A combination of two or more zinc compounds may be mixed in the metal surface treatment liquid. The content of the zinc compound in the metal surface treatment liquid is preferably 0.01 to 5% by mass, and more preferably 0.02 to 3% by mass.

The dissolved oxygen concentration of the metal surface treatment liquid is not particularly limited, but is preferably 0.1% by mass or less. The dissolved oxygen concentration is more preferably 8 ppm by mass or less, and still more preferably 4 ppm by mass or less. When the metal surface treatment liquid contains a large amount of the dissolved oxygen, corrosion and migration are likely to occur on a surface of metal after a surface treatment with the metal surface treatment liquid.

The method for reducing the dissolved oxygen concentration of the metal surface treatment liquid is not particularly limited. Examples of the method for reducing the dissolved oxygen concentration include methods such as bubbling of an inert gas, vacuum degassing, and oxygen deprivation using a polymer film or an inorganic film. The dissolved oxygen concentration of the metal surface treatment liquid can be measured by a well-known method.

<<Surface Treatment Method>>

The third aspect of the present invention is directed to a metal surface treatment method using the above-mentioned metal surface treatment liquid. The metal surface treatment method is performed by bringing metal with the above-mentioned metal surface treatment liquid.

The method for bringing metal into contact with the metal surface treatment liquid is not particularly limited. Examples of the method for bringing metal into contact with a metal surface treatment liquid include a method in which metal is immersed in a metal surface treatment liquid, a method in which a metal surface treatment liquid is coated on a surface of metal, a method in which a metal surface treatment liquid is sprayed over a surface of metal and the like.

When the metal is a wiring formed on a substrate, the method for bringing metal into contact with a metal surface treatment liquid is preferably coating of a metal surface treatment liquid on a substrate surface. Examples of the coating method include a spray coating method, a dip coating method, a roll coating method, a curtain coating method, a spin coating method, a screening printing method, a doctor blade method, an applicator method, and the like.

The conditions such as temperature and time when bringing metal into contact with a metal surface treatment liquid are not particularly limited, as long as the conditions allow a chemical conversion coating film to be formed in a satisfactory manner. The temperature is, for example, preferably 10 to 180° C., and more preferably 30 to 110° C. The time is preferably 20 to 300 seconds, and more preferably 30 to 120 seconds.

In general, after conducting a surface treatment with a metal surface treatment liquid, a solvent derived from the metal surface treatment liquid adhered to the metal is removed. The method for removing a solvent is not particularly limited. Examples thereof include a method in which a solvent is removed by drying with heating, a method in which a surface of metal is washed with a solvent which is easy to be dried, and then the surface of the metal is dried, and the like.

For example, after the wiring made of metal is surface-treated by way of the method as described above, a resist pattern may be formed on the surface-treated wiring, for the purpose of forming a patterned insulating layer on a surface of the wiring, or forming a mold for forming a terminal such as a metal post on the wiring. The type of resist composition used for forming a resist pattern is not particularly limited; and a type of resist composition is appropriately selected depending on the purpose for forming a resist pattern.

When forming a resist pattern, the wiring may be heated by a prebaking step or a post baking step in some cases. However, even when the wiring is heated, as long as the wiring is surface-treated by the above-mentioned methods, infiltration of a metal compound produced by migration into a resist pattern of dendritic crystals, and oxidation of a surface of the wiring are suppressed.

<<Method for Producing Laminate>>

The fourth and fifth aspects of the present invention are directed to a method for producing a laminate.

In the fourth aspect, a laminate is produced by a method including: a chemical conversion coating film formation step of bringing a wired substrate, the wired substrate including a substrate and a wiring made of metal to be disposed on the substrate, into contact with the metal surface treatment liquid mentioned above, thereby forming a chemical conversion coating film on a surface of the wiring; and an insulating layer formation step of forming an insulating layer on a surface provided with the chemical conversion coating film of the wired substrate.

In the fifth aspect, a laminate is produced by a method including: a chemical conversion coating film formation step of bringing a laminate provided with an exposed wiring, the laminate including a substrate, a wiring made of metal to be disposed on the substrate, and an insulating layer which is disposed on the substrate and covers the wiring so that the wiring is partially exposed, into contact with the metal surface treatment liquid mentioned above, thereby forming a chemical conversion coating film on a surface of the wiring exposed from the insulating layer.

Examples of the laminate produced by these methods include a multilayer wiring substrate, a laminated TFT array, and the like. In case where these laminates are produced, the wiring made of metal is often heated to a temperature of about 50 to 300° C. in the step of forming an insulating layer. However, if a chemical conversion coating film is formed in advance on a surface of the wiring using the above-mentioned metal surface treatment liquid when a laminate is produced, it is possible to suppress corrosion of a surface of the wiring, and occurrence of short circuit of the wiring as a result of formation of dendritic crystals of a metal compound due to migration.

The substrate that supports the wiring made of metal is usually an insulating substrate. Examples of the insulating substrate include an organic substrate, a ceramic substrate, a silicon substrate, a glass substrate, and the like. The material of the organic substrate is not particularly limited; and thermocurable resins such as a phenol resin, a urea resin, a melamine resin, an alkyd resin, and an epoxy resin may be used, or thermoplastic resins such as a polyimide resin, a polyphenylene oxide resin, a polyphenylene sulfide resin, an aramid resin, and a liquid crystal polymer may be used. It is also possible to suitably use, as the substrate, a material obtained by impregnating a woven fabric or non-woven fabric made of a glass fiber, an aramid fiber, or an aromatic polyamide fiber with a thermocurable resin, followed by curing.

A width and a thickness of the wiring as well as a distance between the wirings are not particularly limited, but are each preferably 0.1 to 1,000 μm, and more preferably 0.3 to 25 μm. When the laminate is a printed wiring board, the width, the thickness, and the distance between wirings of the wiring are each preferably 1 to 1,000 μm, and more preferably 3 to 25 μm.

The surface treatment with a metal surface treatment liquid targets on a wired substrate or a laminate provided with an exposed wiring, which may include another metal wiring and an interlayer insulating layer in this order, on a surface opposite to the surface provided with the wiring to be surface-treated on the substrate supporting the wire. Note that a plurality of other metal wirings and interlayer insulating layers may be alternatively laminated.

The material of the interlayer insulating layer is not particularly limited; and examples thereof include a phenol resin, a naphthalene resin, a urea resin, an amino resin, an alkyd resin, an epoxy resin, an acrylic resin, and the like.

The laminate provided with the exposed wiring has an insulating layer, in which the insulating layer is disposed on the substrate and covers the wiring so that the wiring is partially exposed. Such an insulating layer is formed by using, for example, an epoxy resin, an aramid resin, a crystalline polyolefin resin, an amorphous polyolefin resin, a fluorine-containing resin, a polyimide resin, a polyethersunfone resin, a polyphenylene sulfide resin, a polyether ether ketone resin, an acrylate resin, or the like. The insulating layer having an opening to expose the wiring is formed by way of, for example, a screening printing method, photolithography using a photosensitive resin composition, or the like.

The wired substrate or the laminate provided with an exposed wiring described above is brought into contact with the above-mentioned metal surface treatment liquid, thereby forming a chemical conversion coating film on a surface of the wiring. The conditions of the surface treatment for forming the chemical conversion coating film are the same as the conditions described above in relation to the surface treatment method according to the third aspect.

After the chemical conversion coating film is formed by using the metal surface treatment liquid, the solvent derived from the metal surface treatment liquid and adhering to the surface of the wired substrate or the laminate provided with an exposed wiring is removed. The method for removing the solvent derived from the metal surface treatment liquid is the same as the method described above in relation to the surface treatment method according to the third aspect.

In the fourth aspect, after a chemical conversion coating film is formed on the wiring on the wired substrate, an insulating layer is formed on a surface provided with the chemical conversion coating film of the wired substrate. Such an insulating layer is formed by, for example, using an epoxy resin, an aramid resin, a crystalline polyolefin resin, an amorphous polyolefin resin, a fluorine-containing resin, a polyimide resin, a polyethersunfone resin, a polyphenylene sulfide resin, a polyether ether ketone resin, an acrylate resin, or the like. The method for forming an insulating layer include is not particularly limited; and examples thereof include a method in which a film for forming an insulating layer is laminated on a substrate, a method in which a composition for forming an insulating layer is coated on a substrate surface, and the like.

The insulating layer may be formed by using a metal surface treatment liquid containing a compound represented by the formula (1a) and the above-mentioned resin which is suitably used for forming an insulating layer. In this case, after a chemical conversion coating film is formed on the wired substrate, an insulating layer can be formed by removing the solvent from the coating film of the metal surface treatment liquid.

Further, an insulating layer can also be formed by using a metal surface treatment liquid composed of a photoresist composition containing an imidazole compound represented by the formula (1a). In this case, after a chemical conversion coating film is formed on a wired substrate by using a metal surface treatment liquid which is a photoresist composition, the solvent is removed from the coating film of the metal surface treatment liquid, and subsequently the coating film is patterned by photolithography, thereby making it possible to form a photoresist pattern with a desired shape as an insulating film on the wired substrate.

The film thickness of the insulating layer to be formed on a surface of the wired substrate is not particularly limited, as long as the wiring can be insulated in a satisfactory manner. When the laminate is a printed wiring board, the thickness of the insulating layer is preferably 5 to 50 μm, and more preferably 15 to 40 μm.

The laminate thus produced suppresses oxidation of a surface of the wiring made of metal, and occurrence of short circuit between wirings arising from formation of dendritic crystals of a metal compound due to migration. Therefore, the laminated produced by way of the method described above is suitably used in various applications.

EXAMPLES

Example 1-1

In Example 1-1, an imidazole compound having the following structure was synthesized as an additive 1.

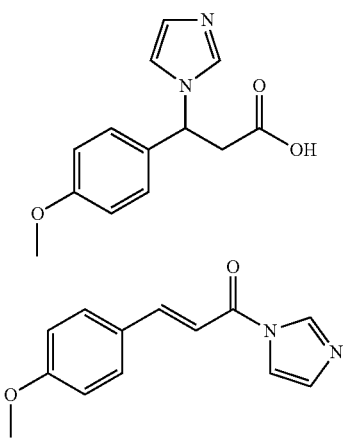

In a dryer, 400 g of a raw material compound having a structure of the above formula (1-(3-(4-methoxyphenyl) acryloyl)-imidazole) was charged together with water, and then heated at 60° C. for a month. The reaction product was subjected to repulp washing with 4,000 g of ethyl acetate at room temperature, followed by filtration and further rinsing twice with 400 g of ethyl acetate to obtain a wet powder 1. The wet powder 1 was subjected again to repulp washing with 4,000 g of ethyl acetate at room temperature, followed by filtration and further rinsing twice with 400 g of ethyl acetate to obtain a wet powder 2. The wet powder 2 was dried under reduced pressure at 40° C. to obtain 300 g of the above objective additive 1 (3-imidazolyl-3-(4-methoxyphenyl)-propionic acid). As a result of the measurement by HPLC, the additive 1 showed a purity of 99.9% or more. The results of the measurement of $^1$H-NMR were as follows.

$^1$H-NMR (DMSO-d6):7.82(1H), 7.31-7.40(3H), 6.88-6.95(2H), 6.85(1H), 5.67-5.70(1H)3.70(3H), 3.16-3.32(2H).

The purity of the additive 1 was measured by the following procedure. After weighing 0.01 to 0.02 g of a crystal of the additive 1 and diluting to 50 mL with acetonitrile (manufactured by Wako Pure Chemical Industries, Ltd., high-performance liquid chromatograph) to obtain a sample, the purity was measured using high-performance liquid chromatography (HPLC). The purity was calculated from a ratio (%) of a peak area of the object compound to the sum total of a peak area of all components observed on a chromatogram.

Analysis conditions of high-performance liquid chromatography are as follows.

<Analysis Conditions>
Column: Inertsil ODS3
Mobile Phase: Liquid A; 50 mM $KH_2PO_4/K_2HPO_4$ (pH=7) aqueous solution
Liquid B; Acetonitrile
Pump Mode: Isocratic (liquid A/liquid B=50%/50% (v/v))
UV wavelength: 220 nm
Injection Amount: 5 μm
Column Temperature: 40° C.
Flow Rate: 1.0 mL/min.

In the measurement of NMR, AVANCE500 NMR Spectrometer manufactured by Bruker Biospin Inc. was used.

Example 1-2

In the same manner as in Example 1-1, except that 4 g of imidazole was added to 400 g of the raw material compound and the heating time was changed to two weeks from a month, 380 g of an additive 1 was obtained. As a result of the measurement by HPLC, the additive 1 showed a purity of 99.9% or more.

Example 1-3

First, 30 g of the raw material compound used in Example 1-1 was dissolved in 200 g of methanol, and 7 g of potassium hydroxide was added in methanol. Then, the methanol solution was stirred at 40° C. After distilling off methanol, the residue was suspended in 200 g of water. The suspension thus obtained was mixed with 200 g of tetrahydrofuran, followed by stirring and further separation of an aqueous phase. Under ice cooling, 4 g of hydrochloric acid was added. After stirring, 100 g of ethyl acetate was mixed, followed by stirring. After the mixed solution was left to stand, an oil phase was separated. The objective product was crystallized from the oil phase, and the precipitate was recovered to obtain an additive 1.

Example 2

In Example 2, an imidazole compound having the following structure was synthesized as an additive 2.

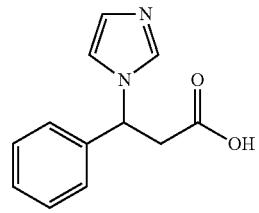 [SMILES: O=C(O)CC(c1ccccc1)n1ccnc1]

Specifically, in the same manner as in Example 1-3, except that the raw material compound was changed to a cinnamic acid derivative having the following structure, an imidazole compound having the above structure (additive 2) was obtained.

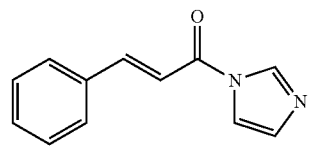 [SMILES: O=C(/C=C/c1ccccc1)n1ccnc1]

Examples 3 to 14 and Comparative Examples 1 to 24

(Preparation of Treatment Solution)

In the solvents of the types shown in Table 1, the additives of the types shown in Table 1 were added so that the concentration of each additive became 2% by mass, and then each additive was uniformly dissolved in each solvent to prepare treatment solutions to be used in the respective Examples and Comparative Examples. Note that the treatment solutions used in Comparative Examples 19 to 24 contain no additive. PGMEA shown in Table 1 is propylene glycol monomethyl ether acetate, and TMU is N,N,N',N'-tetramethylurea.

Additives 1 to 5 shown in Table 1 are mentioned below.
Additive 1: Imidazole compound obtained in Example 1 mentioned above
Additive 2: Imidazole compound obtained in Example 2 mentioned above
Additive 3: Irganox 1010 (manufactured by BASF, pentaerythritol tetrakis[3-(3,5-di-tert-butyl-4-hydroxyphenyl) propionate])
Additive 4: 4-Hydroxy-3,5-di-tert-butyltoluene
Additive 5: Dicyandiamide A substrate (10 cm square) provided with a copper film layer having a thickness of about 4,000 Å formed on a metal substrate made of a Mo—Ti alloy was treated with a treatment solution. Specifically, first, the treatment solution was coated on a surface of the copper film layer using a spin coater. After the coating, the substrate was baked at 100° C. for 100 seconds to remove the solvent in the coating film. After the baking at 100° C., a cross-section of the substrate was observed using a scanning electron microscope. As a result, it has been found that, in the substrate treated with the treatment solution containing an additive, a layer having a thickness of 1,500 to 2,000 Å, which is considered to be derived from the additive in the treatment solution, is formed on the copper film layer.

In Examples 3 to 8, Comparative Examples 1 to 9, and Comparative Examples 19 to 21, after the baking at 100° C., the substrate was further baked at 230° C. for 20 minutes.

In Examples 9 to 14, Comparative Examples 10 to 18, and Comparative Examples 22 to 24, after the baking at 100° C., a resist film was formed on a copper film layer. In formation of a resist film, a resist composition containing a novolac-type resin and a naphthoquinone diazide-type photosensitizer was used.

The resist film was formed by the following procedure. Specifically, first, a resist composition was coated on the copper film layer by a spin coating method, and then prebaked under the condition at 100° C. for 100 seconds. After prebaking, the coating film was exposed at exposure dose of 75 mJ/cm². The coating film thus exposed was developed with an aqueous solution of tetramethyl ammonium hydroxide in the concentration of 2.58% by mass. After the development, the substrate was postbaked at 230° C. for 20 minutes to form a resist film having a predetermined pattern.

After the baking at 230° C., a cross-section of the substrate was observed using a scanning electron microscope, and it was observed whether an oxide film is formed. When the oxide film is formed, the interface between the copper film layer and the oxide film was clearly observed in the cross-section of the substrate. The film thickness of the oxide film thus formed was determined from scanning electron microscope images, and a formation state of the oxide film was evaluated in accordance with the following criteria. Regarding the respective Examples and Comparative Examples, evaluation results on the oxide film formation are shown in Table 1.

<Evaluation Criteria>
A: No oxide film is formed.
B: A film thickness of an oxide film is less than 50 nm.
C: A film thickness of an oxide film is 50 nm or more.

TABLE 1

| | Additive | Solvent | Resist film | Formation of oxide film |
|---|---|---|---|---|
| Ex. 3 | Additive 1 | PGMEA | Not formed | A |
| Ex. 4 | Additive 1 | TMU | Not formed | A |
| Ex. 5 | Additive 1 | Water | Not formed | A |
| Ex. 6 | Additive 2 | PGMEA | Not formed | B |
| Ex. 7 | Additive 2 | TMU | Not formed | B |
| Ex. 8 | Additive 2 | Water | Not formed | B |
| Ex. 9 | Additive 1 | PGMEA | Formed | A |
| Ex. 10 | Additive 1 | TMU | Formed | A |
| Ex. 11 | Additive 1 | Water | Formed | A |
| Ex. 12 | Additive 2 | PGMEA | Formed | B |
| Ex. 13 | Additive 2 | TMU | Formed | B |
| Ex. 14 | Additive 2 | Water | Formed | B |
| Comp. Ex. 1 | Additive 3 | PGMEA | Not formed | C |
| Comp. Ex. 2 | Additive 3 | TMU | Not formed | C |
| Comp. Ex. 3 | Additive 3 | Water | Not formed | C |
| Comp. Ex. 4 | Additive 4 | PGMEA | Not formed | C |
| Comp. Ex. 5 | Additive 4 | TMU | Not formed | C |
| Comp. Ex. 6 | Additive 4 | Water | Not formed | C |
| Comp. Ex. 7 | Additive 5 | PGMEA | Not formed | C |
| Comp. Ex. 8 | Additive 5 | TMU | Not formed | C |
| Comp. Ex. 9 | Additive 5 | Water | Not formed | C |
| Comp. Ex. 10 | Additive 3 | PGMEA | Formed | C |
| Comp. Ex. 11 | Additive 3 | TMU | Formed | C |
| Comp. Ex. 12 | Additive 3 | Water | Formed | C |
| Comp. Ex. 13 | Additive 4 | PGMEA | Formed | C |
| Comp. Ex. 14 | Additive 4 | TMU | Formed | C |
| Comp. Ex. 15 | Additive 4 | Water | Formed | C |
| Comp. Ex. 16 | Additive 5 | PGMEA | Formed | C |
| Comp. Ex. 17 | Additive 5 | TMU | Formed | C |
| Comp. Ex. 18 | Additive 5 | Water | Formed | C |
| Comp. Ex. 19 | None | PGMEA | Not formed | C |

TABLE 1-continued

| | Additive | Solvent | Resist film | Formation of oxide film |
|---|---|---|---|---|
| Comp. Ex. 20 | None | TMU | Not formed | C |
| Comp. Ex. 21 | None | Water | Not formed | C |
| Comp. Ex. 22 | None | PGMEA | Formed | C |
| Comp. Ex. 23 | None | TMU | Formed | C |
| Comp. Ex. 24 | None | Water | Formed | C |

As is apparent from Table 1, it can be understood that, when a copper film layer is surface-treated with a metal surface treatment liquid containing an imidazole compound represented by the formula (1a) of Examples, even if the copper film layer is heated, oxidization of the copper film layer is less likely to occur. Meanwhile, it can be understood that, according to the Comparative Examples, even when a copper film layer is surface-treated with a metal surface treatment liquid without containing the imidazole compound represented by the formula (1a), oxidization of the copper film layer due to heating cannot be suppressed.

In particular, although additives 3 and 4 used in Comparative Examples 1 to 6 and 10 to 15 are well-known compounds as antioxidants, even when the copper film layer was surface-treated with a metal surface treatment liquid containing the additive 3 and 4, oxidization of the copper film layer due to heating could not be prevented.

Note that, as is apparent from scanning electron microscope images of a cross-section of the substrate baked at 230° C., an oxide film having a thickness of about 1,500 to about 2,500 Å is formed in Comparative Examples 1 to 9, whereby, the film thickness of the copper film layer decreased to about 2,500 to about 3,500 Å from 4,000 Å. Meanwhile, in Examples 3 to 8, the oxide film was scarcely formed, and thus the film thickness of the copper film layer was maintained at about 4,000 Å.

In Examples 8 to 14, infiltration of a copper compound generated on the copper film layer into a resist film of dendritic crystals was not observed. Meanwhile, in Comparative Examples 10 to 18 and Comparative Examples 22 to 24, significant infiltration of a copper compound generated on the copper film layer into a resist film of dendritic crystals was observed.

Examples 15 to 18

Regarding Examples 15 to 17, additives (0.4 g) of the types shown in Table 2 were dissolved in 19.6 g of TMU to prepare metal surface treatment liquids. Regarding Example 18, 0.4 g of an additive 2 and 0.1 g of 1H-benzotriazole-5-carboxylic acid were dissolved in 19.5 g of TMU to prepare a metal surface treatment liquid. 1H-benzotriazole-5-carboxylic acid was added in a metal surface treatment liquid as a basic compound.

The effect of suppressing an oxide film from being formed in a metal film layer of the metal surface treatment liquid thus obtained was confirmed in accordance with the following method.

First, a substrate (10 cm square) provided with a metal film layer, made of metals of the types shown in Table 2, having a thickness of about 4,000 Å formed on a metal substrate made of a Mo—Ti alloy was treated with a treatment solution. Specifically, first, the treatment solution was coated on a surface of the metal film layer using a spin coater. After the coating, the substrate was baked at 100° C.

for 100 seconds to remove the solvent in the coating film. After the baking at 100° C., the substrate was further baked at 230° C. for 20 minutes.

After the baking at 230° C., a cross-section of the substrate was observed using a scanning electron microscope, and it was observed whether an oxide film is formed. When the oxide film is formed, the interface between the metal film layer and the oxide film was clearly observed in the cross-section of the substrate. The film thickness of the oxide film thus formed was determined from scanning electron microscope images, and a formation state of the oxide film was evaluated in accordance with the following criteria. Ratings A to D are preferable evaluation results, and rating E is unpreferable evaluation result. Regarding the respective Examples, evaluation results on the oxide film formation are shown in Table 2.

<Evaluation Criteria>
A: No oxide film is formed.
B: A film thickness of an oxide film is less than 5 nm.
C: A film thickness of an oxide film is 5 nm or more and less than 10 nm.
D: A film thickness of an oxide film is 10 nm or more and less than 50 nm.
E: A film thickness of an oxide film is 50 nm or more.

TABLE 2

|  | Additive | Basic compound | Type of metal composing the metal film | Formation of oxide film |
| --- | --- | --- | --- | --- |
| Ex. 15 | Additive 1 | Not added | Ag | B |
| Ex. 16 | Additive 1 | Not added | Al | B |
| Ex. 17 | Additive 1 | Not added | Fe | C |
| Ex. 18 | Additive 2 | Added | Cu | A |

As is apparent from Examples 15 to 17, it can be understood that a treatment with a metal surface treatment liquid containing an imidazole compound represented by the formula (1a) can suppress an oxide film from being formed in relation to various metals.

According to Example 18, it can be understood that the addition of a basic compound such as 1H-benzotriazole-5-carboxylic acid to the metal surface treatment liquid can enhance the effect of suppressing an oxide film from being formed.

Examples 19 to 34 and Comparative Examples 25 to 33

In Examples 19 to 22 and 24 to 34, solutions (2 g) prepared by dissolving additives (0.4 g) of the types shown in Table 3 in solvents of the types shown in Table 3 were added to photoresist compositions of the types shown in Table 3, each containing 19.6 g of a solid component, to obtain metal surface treatment liquids as photoresist compositions.

Abbreviations regarding solvents in Table 3 mean the following solvents.
NMP: N-methyl-2-pyrrolidone
DMAc: N,N-dimethylacetamide
DMIB: N,N-2-trimethylpropaneamide In Example 23, 2.5 g of a solution prepared by dissolving 0.4 g of additives of the types shown in Table 3 and 0.1 g of 1H-benzotriazole-5-carboxylic acid in solvents of the types shown in Table 3 was added to photoresist compositions of the types shown in Table 3, each containing 19.6 g of a solid component, to obtain metal surface treatment liquids as photoresist compositions.

In Comparative Examples 25 to 28, solvents (2 g) of the types shown in Table 3 were added to photoresist compositions of the types shown in Table 3, each containing 19.6 g of a solid component, to obtain metal surface treatment liquids as photoresist compositions.

In Comparative Examples 29 to 32, solutions (2 g) prepared by dissolving additives (0.4 g) of the types shown in Table 3 in solvents of the types shown in Table 3 were added to photoresist compositions of the types shown in Table 3, each containing 19.6 g of a solid component, to obtain metal surface treatment liquids as photoresist compositions. Note that additive 6 used in Comparative Examples 32 is 2-ethyl-4-methyl-1H-imidazole.

In Comparative Examples 33, 2 g of a solution prepared by dissolving 0.4 g of 1H-benzotriazole-5-carboxylic acid in solvents of the types shown in Table 3 was added to photoresist compositions of the types shown in Table 3, each containing 19.6 g of a solid component, to obtain metal surface treatment liquids as photoresist compositions.

The compositions of photoresists PR1 to PR6 used in Examples 19 to 34 and Comparative Examples 25 to 33 are as follows.

[PR1]
PR1 is a negative photoresist composition prepared by diluting 60 parts by mass of a resin having the following structure as an alkali-soluble resin, 33 parts by mass of dipentaerythritol hexaacrylate as a photopolymerizable compound, and 5 parts by mass of 1,2-octanedione,1-[4-(phenylthio)-,2-(O-benzoyloxime)] as a radical polymerization initiator with PGMEA so that the solid component concentration becomes 20% by mass. In the following formula, the numeral at the lower-right hand of parentheses represents a ratio of mass of each structural unit constituting an alkali-soluble resin to total mass of the alkali-soluble resin.
(Alkali-Soluble Resin)

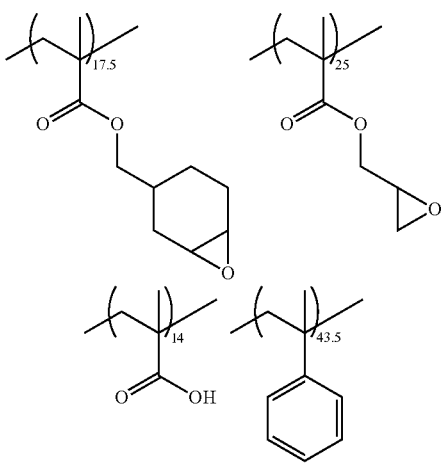

[PR2]
PR2 is a positive photoresist composition having the solid component concentration of 49.5% by mass, prepared by dissolving 20 parts by mass of a novolac resin A1, 55 parts by mass of a novolac resin A2, 8 parts by mass of a crosslinking agent, 14 parts by mass of a photosensitizer, and 1 part by mass of a silane coupling agent in a mixed solvent of 50 parts by mass of diethylene glycol methyl ethyl ether (MEDG) and 50 parts by mass of PGMEA. The respective components included in PR2 will be described below.

(Novolac Resins A1 and A2)

As the novolac resins A1 and A2, resins obtained by the following method were used. Using m-cresol and p-cresol at a ratio of 6:4, formaldehyde and a catalytic amount of oxalic acid were charged and a reaction was performed under reflux, and the reaction time was adjusted, thereby obtaining a novolac resin A1 having a mass average molecular weight of 5,000 in terms of polystyrene, and a novolac resin A2 having a mass average molecular weight of 15,000.

The mass average molecular weight in terms of polystyrene was determined by the following procedure. Using a measuring device (Shodex SYSTEM21, manufactured by Shodex), 20 µl of a sample having the concentration of 0.02 g/10 ml THF was injected into a column (Shodex KF-G, KF-801, manufactured by Shodex). The measurement was made in a column oven at 40° C. by detecting UV absorption at 280 nm while allowing tetrahydrofuran (THF) as an eluent to flow at a flow rate of 1.0 mL/min.

(Photosensitizer)

A partial ester (one of three R(s) is a hydrogen atom) of 1,2-naphthoquinone diazido-5-sulfonic acid of the following 2,3,4,4'-tetrahydroxybenzophenone was used as a photosensitizer.

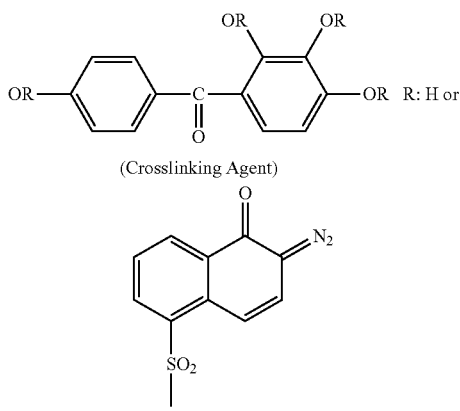

(Crosslinking Agent)

A methylated product of hexamethlolmelamine having the following chemical structure (NIKALAC MW-100LM, manufactured by Sanwa Chemical Co., Ltd.) was used as a crosslinking agent.

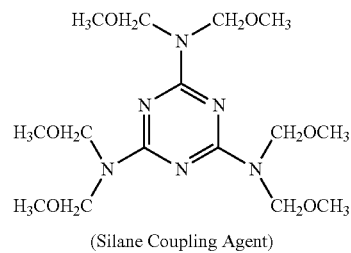

(Silane Coupling Agent)

3-Glycidyloxypropyltrimethoxysilane was used as a silane coupling agent.

[PR3]

PR3 is a positive photoresist composition prepared by dissolving 70 parts by mass of the following photodegradable resin, 30 parts by mass of the following alkali-soluble resin, and 5 parts by mass of a compound having the following structure, which generates an acid or a radical by an action of light in PGMEA so that the solid component concentration becomes 25% by mass. As the photodegradable resin whose protecting group is deprotected under exposure, a resin having the following structure was used. As the alkali-soluble resin, a resin having the following structure was used. In the structural formula regarding the resin, the numeral at the lower-right hand of parentheses represents a ratio of mass of each structural unit to total mass of each resin.

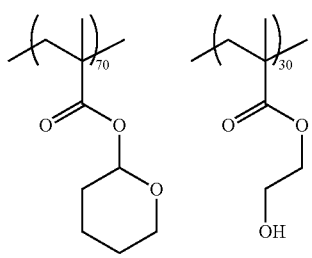

(Photodegradable Resin)

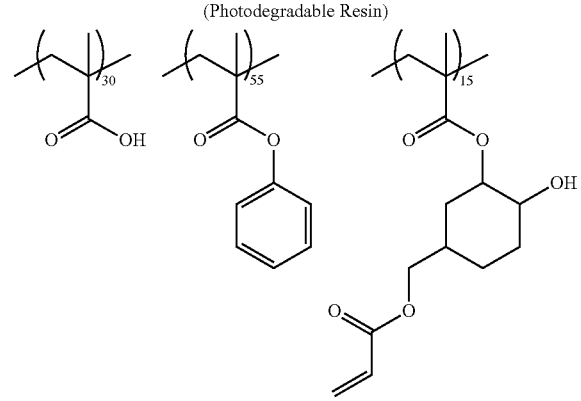

(Alkali-Soluble Resin)

(Compound Capable of Generating Acid or Radical by Action of Light)

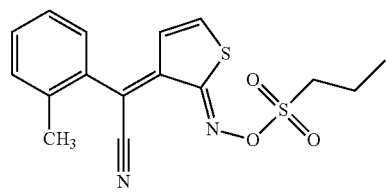 [SMILES: CCCS(=O)(=O)O/N=C1\SC=C\C1=C(\C#N)c1ccccc1C]

[PR4]

PR4 is a positive photoresist composition prepared by dissolving 100 parts by mass of acrylic resin having the following structure, 4 parts by mass of a photoacid generator 1 having the following structure, 10 parts by mass of a photoacid generator 2 having the following structure, and 1 part by mass of salicylic acid in a mixed solvent of 976 parts by mass of propylene glycol monomethyl ether (PGME) and 1464 parts by mass of PGMEA. The mass average molecular weight Mw of acrylic resin is 7,600, and a ratio Mw/Mn of the number average molecular weight Mn and the mass average molecular weight Mw is 1.6. In the following structural formula regarding acrylic resin, the numeral at the lower-right hand of parentheses represents a ratio of mass of each structural unit to total mass of acrylic resin.

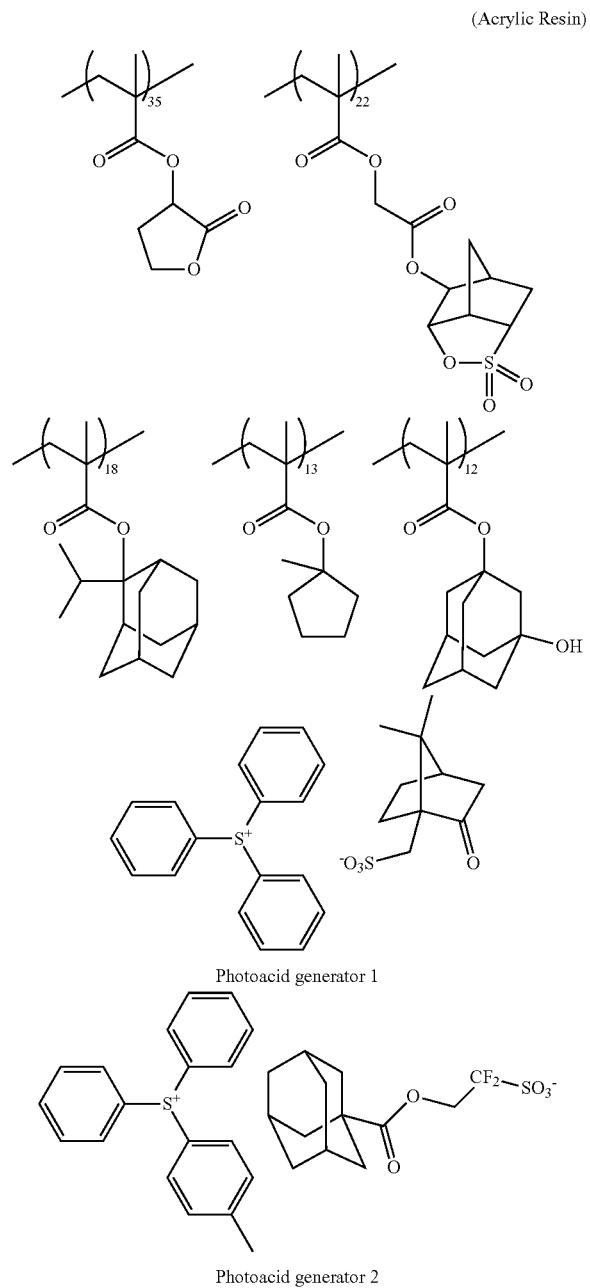

(Acrylic Resin)

Photoacid generator 1

Photoacid generator 2

[PR5]

PR5 is a positive photoresist composition prepared by dissolving 3 parts by mass of the following polyhydroxystyrene A, 7 parts by mass of the following polyhydroxystyrene B, 0.4 part by mass of bis(cyclohexylsulfonyl)diazomethane, 0.1 part by mass of bis(2,4-dimethylphenylsulfonyl) diazomethane, 0.2 part by mass of pyrogallol trimesylate, 0.02 part by mass of salicylic acid, 0.1 part by mass of benzophenone, 0.03 part by mass of triethylamine, and 0.5 part by mass of DMAc in 45 parts by mass of PGMEA.

(Polyhydroxystyrene A)

Polyhydroxystyrene A is a poly(hydroxystyrene) in which 39% of hydroxy groups are substituted with a tert-butoxycarbonyloxy group. Mass average molecular weight of polyhydroxystyrene A is 13,000 and Molecular weight distribution (Mw/Mn) of polyhydroxystyrene A is 1.5

(Polyhydroxystyrene B)

Polyhydroxystyrene B is a Poly(hydroxystyrene) in which 39% of hydroxy groups are substituted with 1-ethoxyethoxy group. Mass average molecular weight of polyhydroxystyrene B is 13,000 and molecular weight distribution (Mw/Mn) of polyhydroxystyrene B is 1.5

[PR6]

PR6 is a positive photoresist composition prepared by dissolving 50 parts by mass of acrylic resin having the following structure, 50 parts by mass of a novolac polymer (m-cresol:p-cresol=6:4), 2 parts by mass of a photoacid generator having the following structure, and 0.1 part by mass of tripentylamine in PGMEA so that the solid component concentration becomes 50% by mass. In the following structural formula regarding acrylic resin, the numeral at the lower-right hand of parentheses represents a ratio of mass of each structural unit to total mass of acrylic resin.

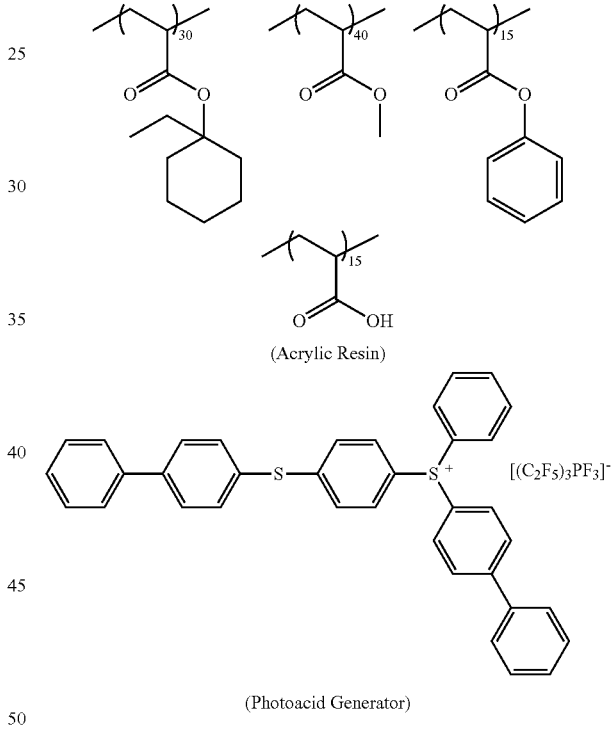

(Acrylic Resin)

(Photoacid Generator)

The effect of suppressing an oxide film from being formed in the metal film layer of the metal surface treatment liquid thus obtained was confirmed by the following method.

First, a substrate (10 cm square) provided with a metal film layer, made of metals of the types shown in Table 3, having a thickness of about 4,000 Å formed on a metal substrate made of a Mo—Ti alloy was treated with a treatment solution. Specifically, first, a treatment solution was coated on a surface of a metal film layer using a spin coater. After the coating, the substrate was baked at 100° C. for 100 seconds to remove the solvent in the coating film. Then, the coating film was patterned in accordance with the method suited for each resist composition by photolithography to form a resist pattern which partially covers the metal film layer. After the resist pattern was formed, the substrate was further baked at 230° C. for 20 minutes.

After the baking at 230° C., a cross-section of the substrate was observed using a scanning electron microscope, and it was observed whether an oxide film is formed. When the oxide film is formed, the interface between the metal film layer and the oxide film was clearly observed in the cross-section of the substrate. The film thickness of the oxide film thus formed was determined from scanning electron microscope images, and a formation state of the oxide film was evaluated in accordance with the following criteria. Ratings A to D are preferable evaluation results, and rating E is unpreferable evaluation result. Regarding the respective Examples and Comparative Examples, evaluation results on the oxide film formation are shown in Table 3.

<Evaluation Criteria>
A: No oxide film is formed.
B: A film thickness of an oxide film is less than 5 nm.
C: A film thickness of an oxide film is 5 nm or more and less than 10 nm.
D: A film thickness of an oxide film is 10 nm or more and less than 50 nm.
E: A film thickness of an oxide film is 50 nm or more.

TABLE 3

| | Type of photoresist | Additive | Diluting solvent | Basic compound | Type of metal composing the metal film | Formation of oxide film |
|---|---|---|---|---|---|---|
| Ex. 19 | PR1 | Additive 1 | PGMEA | Not added | Cu | B |
| Ex. 20 | PR1 | Additive 1 | PGMEA | Not added | Ag | C |
| Ex. 21 | PR1 | Additive 1 | PGMEA | Not added | Al | C |
| Ex. 22 | PR1 | Additive 1 | PGMEA | Not added | Fe | D |
| Ex. 23 | PR1 | Additive 1 | PGMEA | Added | Cu | A |
| Ex. 24 | PR1 | Additive 1 | PGMEA | Not added | Cu | B |
| Ex. 25 | PR1 | Additive 1 | TMU | Not added | Cu | B |
| Ex. 26 | PR1 | Additive 1 | NMP | Not added | Cu | B |
| Ex. 27 | PR1 | Additive 1 | DMAc | Not added | Cu | B |
| Ex. 28 | PR1 | Additive 1 | DMIB | Not added | Cu | B |
| Ex. 29 | PR1 | Additive 2 | PGMEA | Not added | Cu | C |
| Ex. 30 | PR2 | Additive 1 | PGMEA | Not added | Cu | C |
| Ex. 31 | PR3 | Additive 1 | PGMEA | Not added | Cu | B |
| Ex. 35 | PR4 | Additive 1 | PGMEA | Not added | Cu | B |
| Ex. 33 | PR5 | Additive 1 | PGMEA | Not added | Cu | B |
| Ex. 34 | PR6 | Additive 1 | PGMEA | Not added | Cu | B |
| Comp. Ex. 25 | PR1 | — | PGMEA | Not added | Cu | E |
| Comp. Ex. 26 | PR1 | — | PGMEA | Not added | Ag | E |
| Comp. Ex. 27 | PR1 | — | PGMEA | Not added | Al | E |
| Comp. Ex. 28 | PR1 | — | PGMEA | Not added | Fe | E |
| Comp. Ex. 29 | PR1 | Additive 3 | PGMEA | Not added | Cu | E |
| Comp. Ex. 30 | PR1 | Additive 4 | PGMEA | Not added | Cu | E |
| Comp. Ex. 31 | PR1 | Additive 5 | PGMEA | Not added | Cu | E |
| Comp. Ex. 32 | PR1 | Additive 6 | PGMEA | Not added | Cu | E |
| Comp. Ex. 33 | PR1 | — | PGMEA | Added | Cu | E |

According to Examples 19 to 34, it can be understood that, even when the metal surface treatment liquid is a photoresist composition containing a resin, the treatment with the metal surface treatment liquid can satisfactorily suppress an oxide film from being formed. The observation results of a cross-section of the substrate regarding the respective Examples using a scanning electron microscope revealed no significant differences in the effect of suppressing an oxide film from being formed, between the position where a metal film was coated with a resist pattern, and the position where a metal film was not coated with a resist pattern. This is considered to be attributable to a fact that, at the stage where a liquid metal surface treatment agent as a photoresist composition was coated on the substrate, the composition was coordinated to the metal film of an imidazole compound represented by the formula (1a), and a chemical conversion coating film was formed.

As is apparent from a comparison between Example 19 and Example 23, it can be understood that the addition of a basic compound such as 1H-benzotriazole-5-carboxylic acid to the metal surface treatment liquid as the photoresist composition can enhance the effect of suppressing formation of the oxide film.

According to Comparative Examples 25 to 33, it can be understood that, even when a photoresist composition without containing the imidazole compound represented by the formula (1a) is used as a metal surface treatment liquid, oxidization of the oxide film on a surface of the metal film cannot be suppressed.

The invention claimed is:

1. An imidazole compound represented by the following formula (1-1-1):

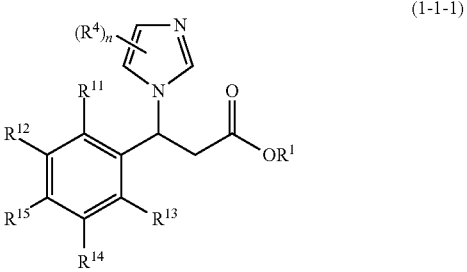

(1-1-1)

wherein $R^1$ represents a hydrogen atom or an alkyl group, $R^4$ represents a halogen atom, a hydroxyl group, a mercapto group, a sulfide group, a silyl group, a silanol group, a nitro group, a nitroso group, a sulfonate group, a phosphino group, a phosphinyl group, a phosphonato group, or an organic group,
   at least one of $R^{11}$, $R^{12}$, $R^{13}$, $R^{14}$, and $R^{15}$ is a group represented by —O—$R^{10}$ wherein $R^{10}$ is an alkyl group, and each remaining member of $R^{11}$, $R^{12}$, $R^{13}$, $R^{14}$, and $R^{15}$ is a hydrogen atom, and
   n represents an integer of 0 to 3.

2. A metal surface treatment liquid comprising the imidazole compound according to claim 1.

3. The metal surface treatment liquid according to claim 2, further comprising a resin.

4. The metal surface treatment liquid according to claim 2, wherein the metal surface treatment liquid is a photoresist composition.

5. The metal surface treatment liquid according claim 2, wherein metal to be treated is copper or an alloy containing copper.

6. A metal surface treatment method, comprising contacting a metal with the metal surface treatment liquid according to claim 2.

7. The metal surface treatment method according to claim 6, wherein the metal is copper or an alloy containing copper.

8. A method for producing a laminate, comprising:
bringing a wired substrate, the wired substrate including a substrate and a wiring made of metal to be disposed on the substrate, into contact with the metal surface treatment liquid according to claim 2, thereby forming a chemical conversion coating film on a surface of the wiring; and
forming an insulating layer on a surface provided with the chemical conversion coating film of the wired substrate.

9. The method for producing a laminate according to claim 8, wherein the metal is copper or an alloy containing copper.

10. A method for producing a laminate, the method comprising:
bringing a laminate with an exposed wiring, the laminate including a substrate, a wiring made of metal to be disposed on the substrate, and an insulating layer which is disposed on the substrate and covers the wiring so that the wiring is partially exposed, into contact with the metal surface treatment liquid according to claim 2, thereby forming a chemical conversion coating film on a surface of the wiring exposed from the insulating layer.

11. The method for producing a laminate according to claim 10, wherein the metal is copper or an alloy containing copper.

12. The imidazole compound according to claim 1, wherein the $R^{11}$, $R^{12}$, $R^{13}$ and $R^{14}$ each represent a hydrogen atom and $R^{15}$ is the group represented by —O—$R^{10}$.

13. The imidazole compound according to claim 1, wherein the $R^1$ represents a hydrogen atom.

14. The imidazole compound according to claim 1, wherein the n represents 0.

15. The imidazole compound according to claim 1, wherein the imidazole compound is a compound represented by the following formula:

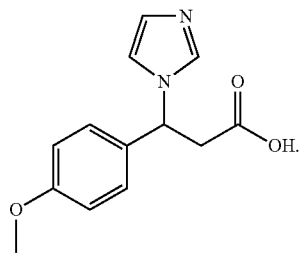 [SMILES: COc1ccc(C(CC(=O)O)n2ccnc2)cc1]

* * * * *